United States Patent
Triplett et al.

(10) Patent No.: US 7,324,744 B2
(45) Date of Patent: Jan. 29, 2008

(54) MULTI-ORIENTATION LOW PROFILE DUAL OUTLET VOLATILE DISPENSER

(75) Inventors: Carl Triplett, Scottsdale, AZ (US); Jeffrey Bankers, Scottsdale, AZ (US); Kevin Hafer, Phoenix, AZ (US); Paul Pappalardo, Scottsdale, AZ (US); Geoffrey Faires, Cave Creek, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 11/424,754

(22) Filed: Jun. 16, 2006

(65) Prior Publication Data

US 2007/0065125 A1 Mar. 22, 2007

Related U.S. Application Data

(63) Continuation of application No. 11/162,393, filed on Sep. 8, 2005, now Pat. No. 7,151,891.

(51) Int. Cl.
*A01G 13/06* (2006.01)

(52) U.S. Cl. .................. 392/386; 392/390; 392/392

(58) Field of Classification Search .............. None
See application file for complete search history.

(56) References Cited

U.S. PATENT DOCUMENTS

| | | | | |
|---|---|---|---|---|
| 3,626,354 A | * | 12/1971 | Banner | 439/105 |
| 3,775,727 A | * | 11/1973 | Wise | 439/105 |
| 4,000,405 A | * | 12/1976 | Horwinski | 362/95 |
| 5,111,477 A | * | 5/1992 | Muderlak et al. | 392/390 |
| 6,085,026 A | * | 7/2000 | Hammons et al. | 392/390 |
| 6,603,924 B2 | * | 8/2003 | Brown et al. | 392/390 |
| 6,714,725 B2 | * | 3/2004 | Grone et al. | 392/392 |
| 6,810,204 B2 | * | 10/2004 | Grone et al. | 392/392 |
| 6,920,282 B2 | * | 7/2005 | He et al. | 392/392 |
| 2002/0172512 A1 | * | 11/2002 | Stathakis et al. | 392/395 |
| 2003/0138241 A1 | * | 7/2003 | Pedrotti et al. | 392/395 |
| 2004/0057706 A1 | * | 3/2004 | Grone et al. | 392/392 |
| 2004/0105667 A1 | * | 6/2004 | He et al. | 392/392 |
| 2004/0247300 A1 | * | 12/2004 | He et al. | 392/390 |
| 2005/0286876 A1 | * | 12/2005 | Gasper | 392/392 |

* cited by examiner

*Primary Examiner*—Thor S. Campbell
(74) *Attorney, Agent, or Firm*—Snell & Wilmer LLP (57) ABSTRACT

The invention provides means within an improved vapor dispensing device to accommodate or compensate for multiple orientations of an outlet into which the device is to be inserted. Orientation compensation is accomplished by inverted and/or rotatable electrical adapters, universal contacts on a base member, enlarged passive dispersion channels, enlarged emanators, multiple emanators, baffles cooperating with an emanator, and/or sleeves encasing multiple wicks to allow for operation of the device in multiple orientations.

10 Claims, 7 Drawing Sheets

MULTI-ORIENTATION LOW PROFILE DUAL OUTLET VOLATILE DISPENSER

CROSS-REFERENCE TO RELATED APPLICATION

This application is a continuation of U.S. Ser. No. 11/162,393 entitled "MULTI-ORIENTATION LOW PROFILE DUAL OUTLET VOLATILE DISPENSER" filed on Sep. 8, 2005 now U.S. Pat. No. 7,151,891, which application is incorporated herein by reference.

FIELD OF INVENTION

This invention generally relates to a vapor-dispensing device, and more particularly to a multiple-outlet vapor dispensing device.

BACKGROUND OF THE INVENTION

Vapor-dispensing devices of the type inserted into common electrical outlets are generally known. Many such devices require a particular positioning or orientation relative to the outlet due to the polar configuration and dimensioning of the electrical prongs and corresponding outlet openings. For example, in the United States, many standard polar two-prong devices include a larger prong and a smaller prong corresponding respectively to the two electrical poles and differentiated openings of the wall outlet. Some devices require that the poles and thus the prongs be aligned for proper operation of the device. Other devices may employ the polar plug design merely to provide improved stability, particularly if the device does not have a third prong for grounding.

Problems may arise, however, when electricians install a polar or other standard outlet upside down, which is sometimes an industry practice used to indicate when the outlet is coupled to a light switch. In such cases, orienting a device having polar prongs with the inverted polar outlet may cause inferior performance, instability or failure of the device. In the case of air fresheners or other devices employing a liquid medium, it is a concern that inversion of the device may result in condensation or leakage of the liquid medium. Furthermore, various dispenser components such as wicks, emanators, or dispersion passages may rely on gravity or may be otherwise dependent on a particular orientation. Similarly, problems may be encountered when a device is plugged into an outlet that is installed horizontally.

Accordingly, there is a need for means to properly orient such devices relative to an inverted outlet and/or for means to render such devices capable of operation in multiple orientations.

SUMMARY OF THE INVENTION

While the way that the present invention addresses the disadvantages of the prior art will be discussed in greater detail below, in general, the present invention provides means associated with a dispensing device for compensating for various orientations of an outlet into which the device is to be inserted.

In accordance with various aspects of the present invention, operational independence of a dispenser and/or reservoir relative to an outlet orientation may be accomplished with a base member configured to be oriented independent of the outlet orientation, a reservoir configured to be oriented independent of a base member orientation, a reservoir and associated dispenser configured to operate in multiple orientations, or a pair of sleeved wicks configured for selective transport of dispersible material based upon device orientation.

BRIEF DESCRIPTION OF THE DRAWINGS

A more complete understanding of the present invention may be derived by referring to the detailed description and claims when considered in connection with the Figures, wherein like reference numerals refer to similar elements throughout the Figures.

DETAILED DESCRIPTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, delivery mechanisms and the like and still fall within the scope of the present invention. Thus, the detailed description herein is presented for purposes of illustration only and not of limitation.

Various outlet orientation compensating means are disclosed herein in the exemplary context of air fresheners. That being said, the present invention may be used with any vapor-dispensing products. Such products typically include a volatizable material and a transport system configured to facilitate evaporation of the volatizable material into the surrounding air. Exemplary volatizable materials include fragrances, air fresheners, deodorizers, odor eliminators, odor counteractants, insecticides, insect repellants, medicinal substances, disinfectants, sanitizers, mood enhancers, and aroma therapy compositions. Thus, "air freshener" as used herein refers to any vapor dispensing device similarly described in connection with polarized dual-outlet receptacles. That being said, such air fresheners may be used in connection with any configuration or orientation of receptacle.

Air fresheners may be passive in operation, i.e., they may operate by ambient evaporation without the need for additional energy input to the system, or they may be active, requiring additional energy input, for example, in the form of heating elements or fans. Conventional air fresheners often include a refillable or replaceable reservoir.

An exemplary air freshener according to the present invention comprises a low profile dispensing device that resembles a standard dual electrical outlet and includes a base member having at least one pair of electrical prongs for insertion into an electrical wall outlet, a secondary electrical outlet, and a heating element for heating a volatile material. A replaceable or refillable reservoir containing volatile material is attachable to the base member and associated with a dispenser, e.g., an emanator pad. The device further includes orientation compensating means allowing for upright orientation of the reservoir, base member, dispenser and/or other components independent of the orientation of the wall outlet (e.g., upright, horizontal, or inverted). "Upright," as used herein refers to a target or default orientation.

Orientational and/or operational independence of the reservoir or dispenser relative to the outlet orientation may be accomplished by numerous configurations. For example, briefly, one embodiment includes a base member configured to be oriented independent of an outlet orientation. Another embodiment includes a reservoir configured to be oriented independent of a base member orientation. Another embodiment includes a reservoir and associated dispenser configured to operate in multiple orientations. Yet another embodiment includes a pair of sleeved wicks configured for alternate operation depending upon orientation. In sum, any number of air freshener components may be configured to accommodate multiple wall outlet orientations or multiple air freshener orientations.

Figure 1:
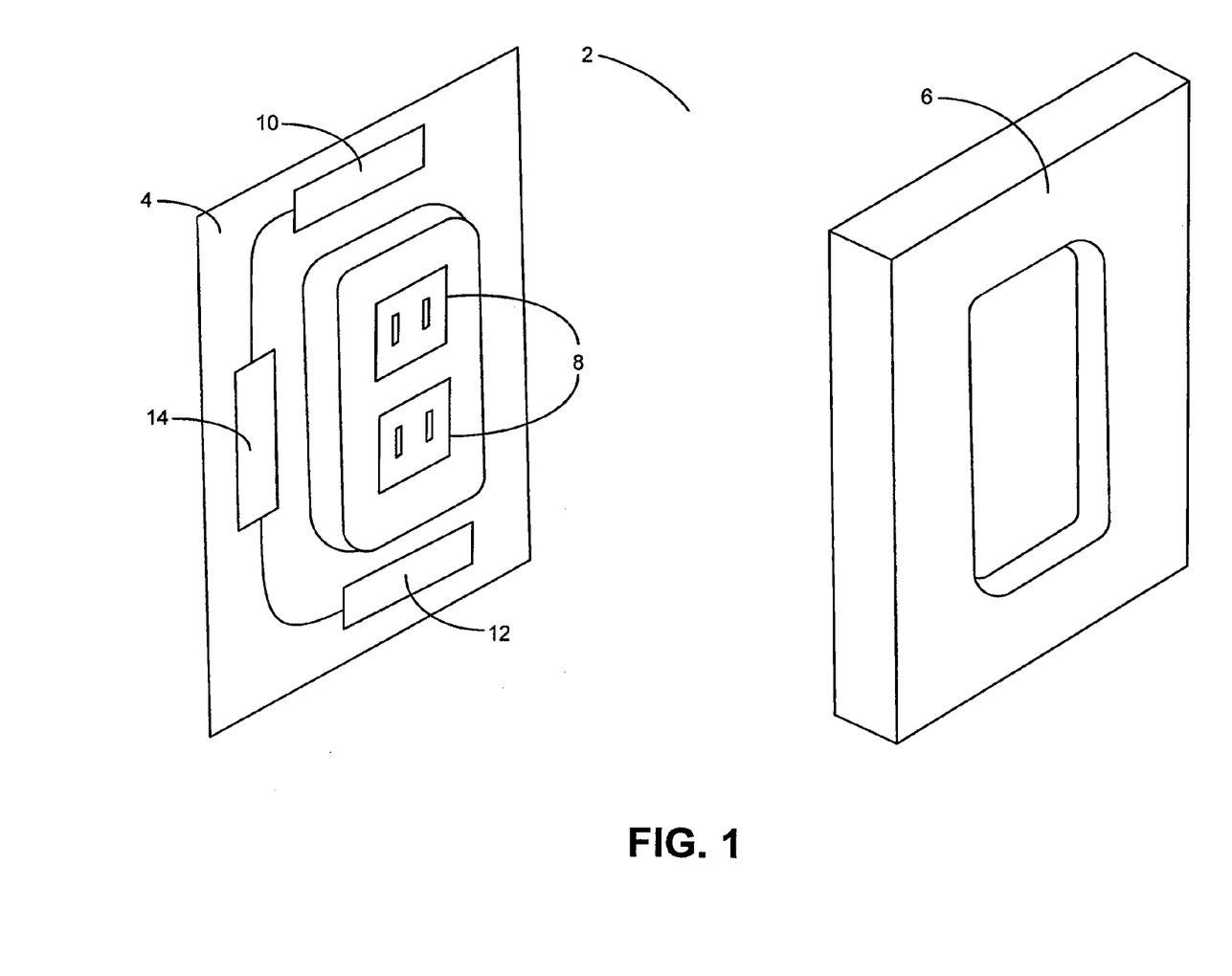
FIG. 1 illustrates an exemplary dispensing device according to one embodiment having an orientation sensor.

For example, with reference to FIG. 1, an exemplary embodiment of an air freshener device 2 includes a base 4, and a reservoir 6. Base 4 includes electrical prongs (not shown) for insertion into a wall outlet, a pair of secondary outlets 8, heating elements 10 and 12, and a gravity switch 14. Heating elements 10 and 12 are electrically connected through gravity switch 14 to the electrical prongs on base 4. Gravity switch 14 is configured to selectively supply power to heating elements 10 and 12 based upon the orientation of base 4. Gravity switch 14 may be activated by a weight or fluid acting under the influence of gravity. For example, heating element 10 may be powered with base 4 in an upright orientation while heating element 12 may be powered with base 4 in an inverted orientation.

In an alternative embodiment, heating elements 10 and 12 may be simultaneously powered regardless of the orientation of base 4. Heating elements 10 and 12 may be further configured to operate periodically or continuously. In another embodiment, selective activation of heating elements 10 and 12 may be manual or automatic through use of any other suitable control or sensor. Any number of heating elements may be used, configured, and located to suitably volatize dispersible materials with the device in multiple orientations.

Figure 2A:
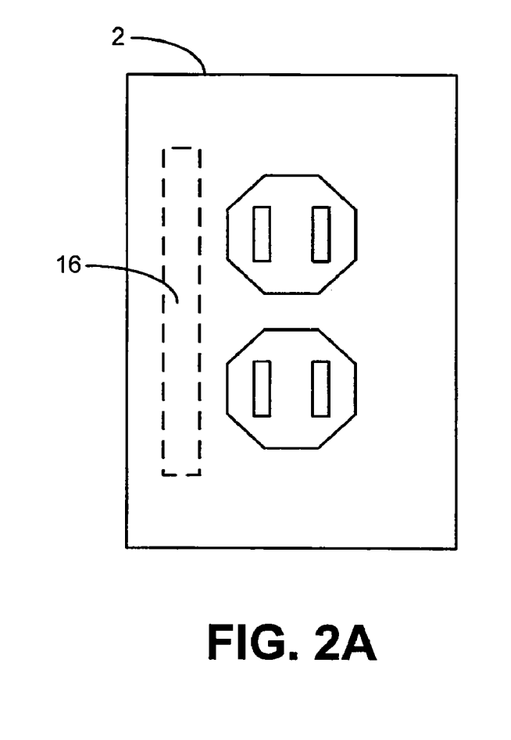
FIGS. 2A-2C illustrate exemplary dispensing devices according to various embodiments having various emanator configurations.
Figure 2B:
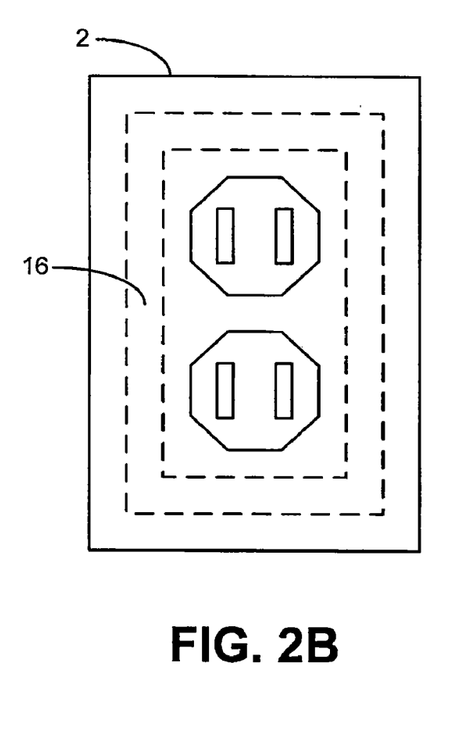
Figure 2C:
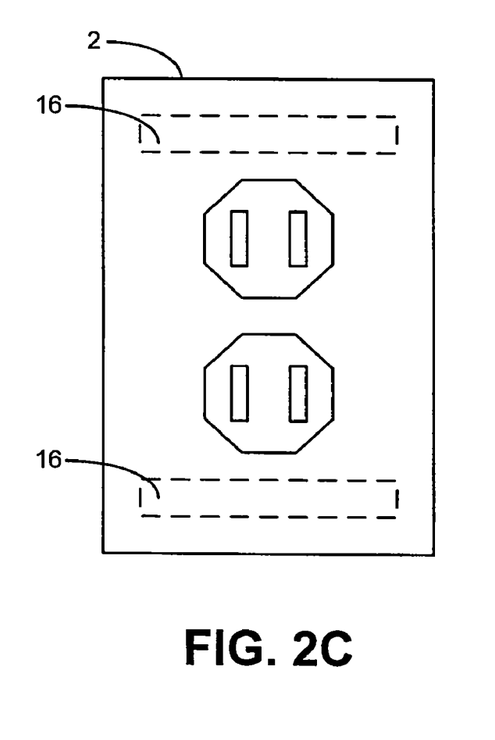

With reference now to FIGS. 2A-2C, another embodiment of device 2 is shown including an emanator 16 configured for multiple or universal orientation(s). Exemplary emanators 16 include an absorbent pad, evaporation surface, porous material or the like. As shown in FIG. 2A, emanator 16 may be disposed along a side portion of reservoir 6 or base 4 and configured to dispense a substantially consistent quantity of volatile material regardless of the orientation of reservoir 6 and/or base 4. For example, emanator 16 may be symmetrically aligned with respect to an axis common to device 2 in multiple orientations. Further to this example, emanator 16 may be supplied by wicks (not shown) extending to either vertical end of reservoir 6, accommodating multiple orientations of reservoir 6.

Alternatively, emanator 16 may be configured in any manner suitable to allow for controlled dispensing of volatile materials with the reservoir in at least an upright and an inverted orientation. For example, as shown in FIG. 2B, emanator 16 may be disposed in multiple locations around the periphery of base 4 or reservoir 6 or may be configured as a substantially continuous ring.

In yet another embodiment shown in FIG. 2C, emanators 16 are placed at each longitudinal end of device 2 for cooperation with heating elements 10 and 12 on base 4, as shown in FIG. 1. As described above, emanators 16 may be selectively supplied with heat and/or volatile material according to the orientation of device 2.

In various other embodiments of device 2, any number of device components may be configured to accommodate various wall outlet or device component orientations. One such exemplary embodiment, includes spacing reservoir 6 a sufficient distance from base 4 to allow sufficient air flow past emanator 16 and/or providing an enlarged emanator 16 to accommodate any excess or variations in the transport or dispersion of volatile materials resulting from the various device orientations. Alternatively, use of a smaller quantity of volatile material, as with a smaller reservoir 6 or smaller emanator 16, may serve to reduce leakage in the event that device 2 is inverted. Similarly, in embodiments employing a wick to transport volatile material from reservoir 6 to emanator 14, the wick may be configured to meter capillary transport regardless of device orientation, for example by altering the composition or porosity of the wick. In another embodiment, the composition of the volatile material may be selected to achieve substantially uniform delivery regardless of orientation, for example, by use of a gel instead of an oil carrier.

Figure 3:
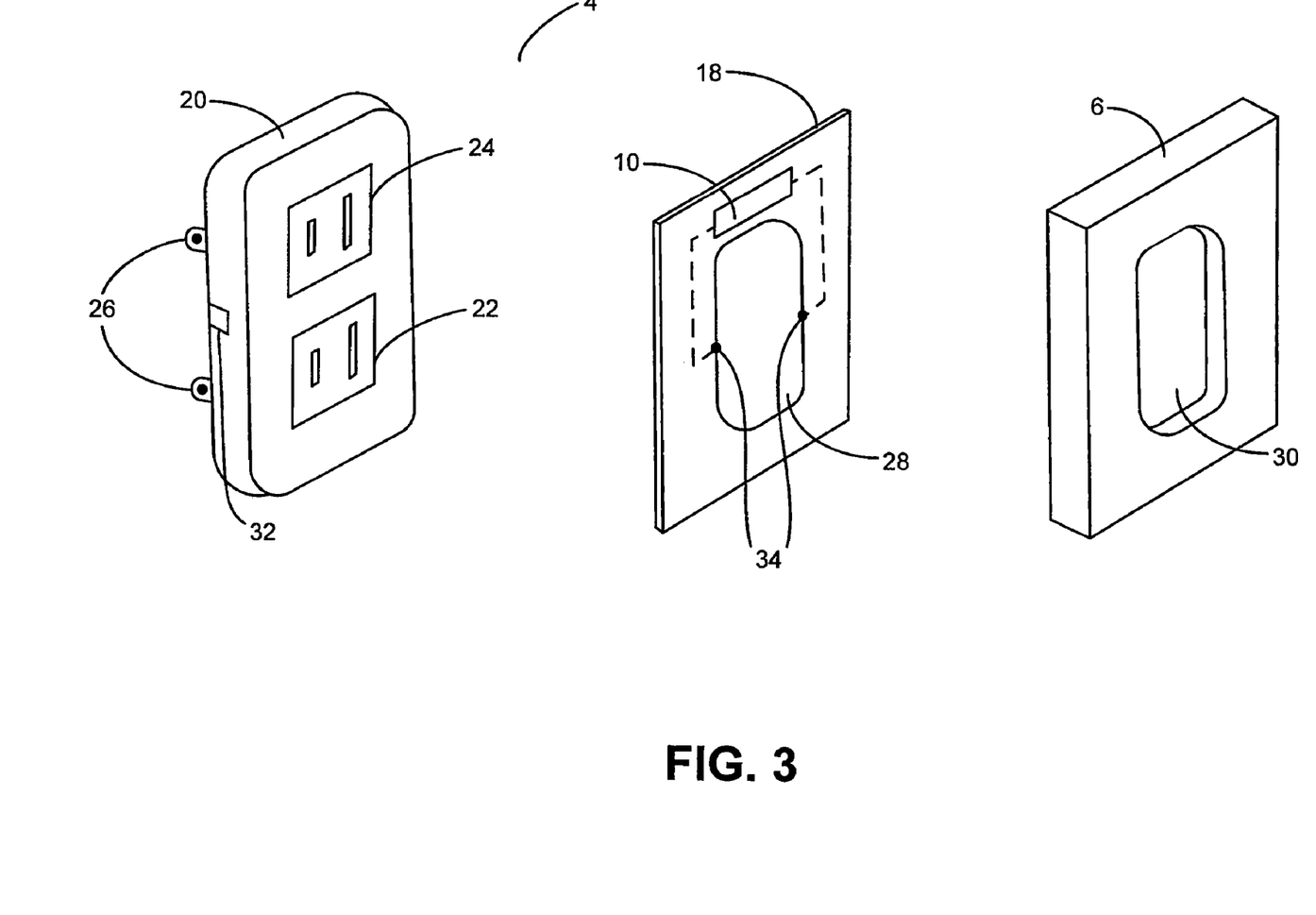
FIG. 3 illustrates an exemplary dispensing device according to an embodiment having a reversible outlet body.

In another embodiment shown in FIG. 3, base 4 is comprised of a base plate 18 and a removable, reversible outlet body 20 having a first polar outlet 22 and a second polar outlet 24 coupled to at least one of a first and second pair of polar prongs 26. Outlet body 20 has a symmetrical profile, e.g., rectangular, and includes electrical outlets 22 and 24. A first symmetrical opening 28 in base plate 18 and a second symmetrical opening 30 in reservoir 6 accommodate the corresponding symmetrical profile of outlet body 18 in both the upright and inverted orientation. Use of a symmetrical outlet body 20 and corresponding opening 28 allows base plate 18 to be attached to outlet body 20 in an upright orientation regardless of whether outlet body 20 is upright or inverted. That being said, any suitable combination of outlet body profiles and complimentary openings 28 and 30 may be used such that outlet prong pairs 26 on outlet body 20 are first inserted into a wall outlet according to the orientation of the wall outlet and then base plate 18 and/or reservoir 6 are then attached to outlet body 20 in the upright position.

With continued reference to FIG. 3, outlet body 20 further includes electrical contacts 32 for communicating power to heating element(s) 10 by means of electrical leads 34 on base plate 18. Electrical contacts 32 are located along a centerline of outlet body 20 to contact heating element leads 34 located along a centerline of base plate 18 with outlet body 20 in either the upright or the inverted position. Thus, reservoir 6 and base plate 18 may both be removable and rotatable relative to outlet body 20.

Electrical leads 34 and electrical contacts 32 may be further configured as the means of attachment between base plate 18 and outlet body 20. This may be accomplished, for example, by configuring electrical contacts 32 to securely receive or otherwise attachably engage heating element leads 34. For example, in one embodiment, electrical leads 34 include protruding posts and electrical contacts 32 include grooves for receiving the protruding posts. Electrical contacts 32 of outlet body 20 and electrical leads 34 of base plate 18 may be configured in any suitable manner to allow for proper orientation of heating element 10 and/or other dispensing mechanism relative to an upright, inverted, or rotated outlet body 20.

Alternatively, base plate 18 or reservoir 6 may be press-fitted, snap-fitted, slidably fitted or otherwise suitably attached to outlet body 20 to cause electrical leads 34 to engage electrical contacts 32. Reservoir 6 and base plate 18 may be separately attachable to outlet body 20. Alternatively, reservoir 6 may attach to base plate 18 and the combination may then attach to outlet body 20. It is understood that reservoir 6, base plate 18, and outlet body 20 may be assembled and attached in any suitable manner. That being said, any of the embodiments described herein may be used with purely passive delivery systems as well, i.e., without the need for heating element 10, electrical contacts 32, electrical leads 34, fans, or the like. For example, a simple wick and emanator 16 associated with reservoir 6 may be maintained upright by any number of means described herein.

In accordance with one embodiment, device 2 is specifically configured to accommodate an inverted outlet by means of inverted polar prongs. This may be done by reversing the positions of the larger and smaller prongs. Thus, a reservoir, emanator, and wick may be maintained upright without further structural modifications.

Figure 4:
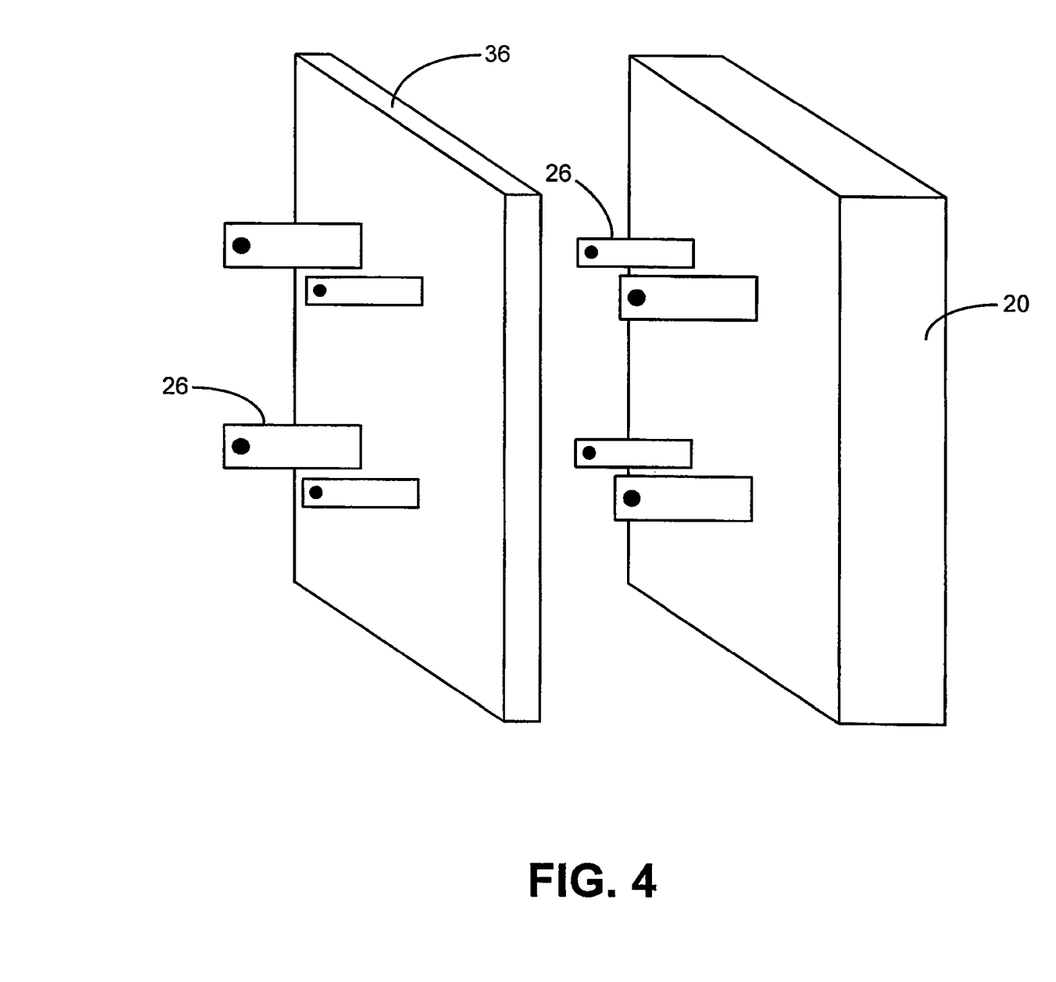
FIG. 4 illustrates an exemplary dispensing device according to an embodiment employing an inverted polar prong adapter.

In another embodiment shown in FIG. 4, outlet body 20 including polar electrical prongs 26 may be maintained in an upright orientation by use of an inverter adapter 36 interposed between the upright outlet body 20 and an inverted wall outlet. Polar electrical prongs 26 on inverted adapter are geometrically inverse to those of outlet body 20 allowing for upright orientation of outlet body 20.

Figure 5:
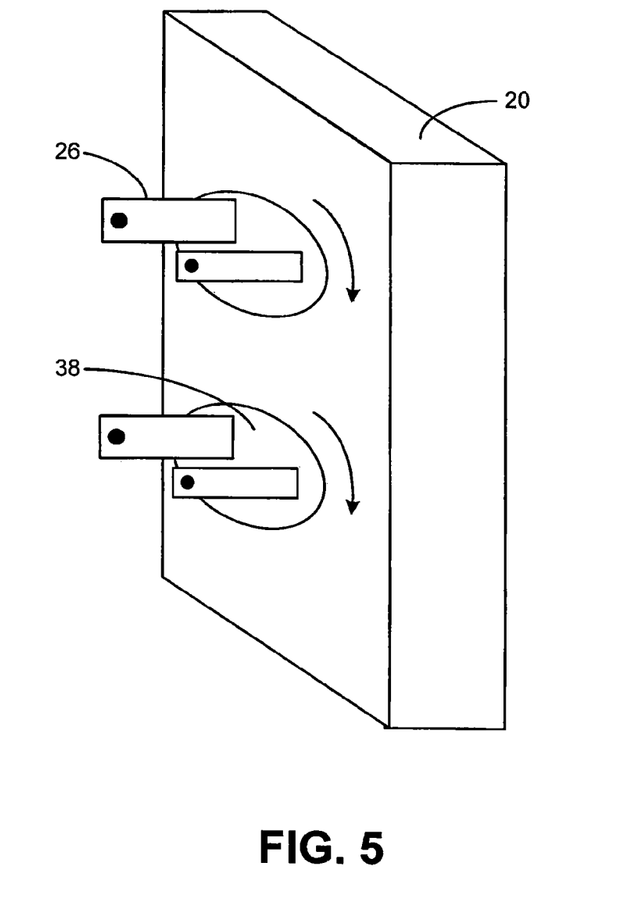
FIG. 5 illustrates an exemplary dispensing device according to an embodiment having rotatable polar prongs.

With reference now to FIG. 5, still another embodiment includes an outlet body 20 having a pair polar prongs 26 integrated into a rotator(s) 38 moveable between multiple positions to allow for multiple orientations of the device relative to a wall outlet. For example, a single pair of polar prongs 26 may be rotated as desired between 0 and 360 degrees, while two pairs of polar prongs may be jointly rotated 180 degrees by turning rotator(s) 38. In another embodiment, two pairs of polar prongs 26 are fixed to a single rotator 38. Any means of reorienting polar prongs 26 with respect to outlet body 20, whether now known or later developed, may be used in conjunction with the present invention.

Another exemplary embodiment includes a baffle(s) adjacent emanator 16 to absorb and/or divert any leaked, condensed, or excess volatile dispersible materials released in a given orientation of the device. Baffles may be associated with emanator 16 or any other dispensing mechanism or other device component. One exemplary baffle is composed of an absorptive material placed in close proximity to emanator 16. Baffle may be any material or structure configured to absorb, stop, divert, or otherwise contain leaked or condensed volatile materials. In one embodiment, baffles are provided on two sides of emanator 16, one to contain leakage, the other to contain condensation.

Figure 6:
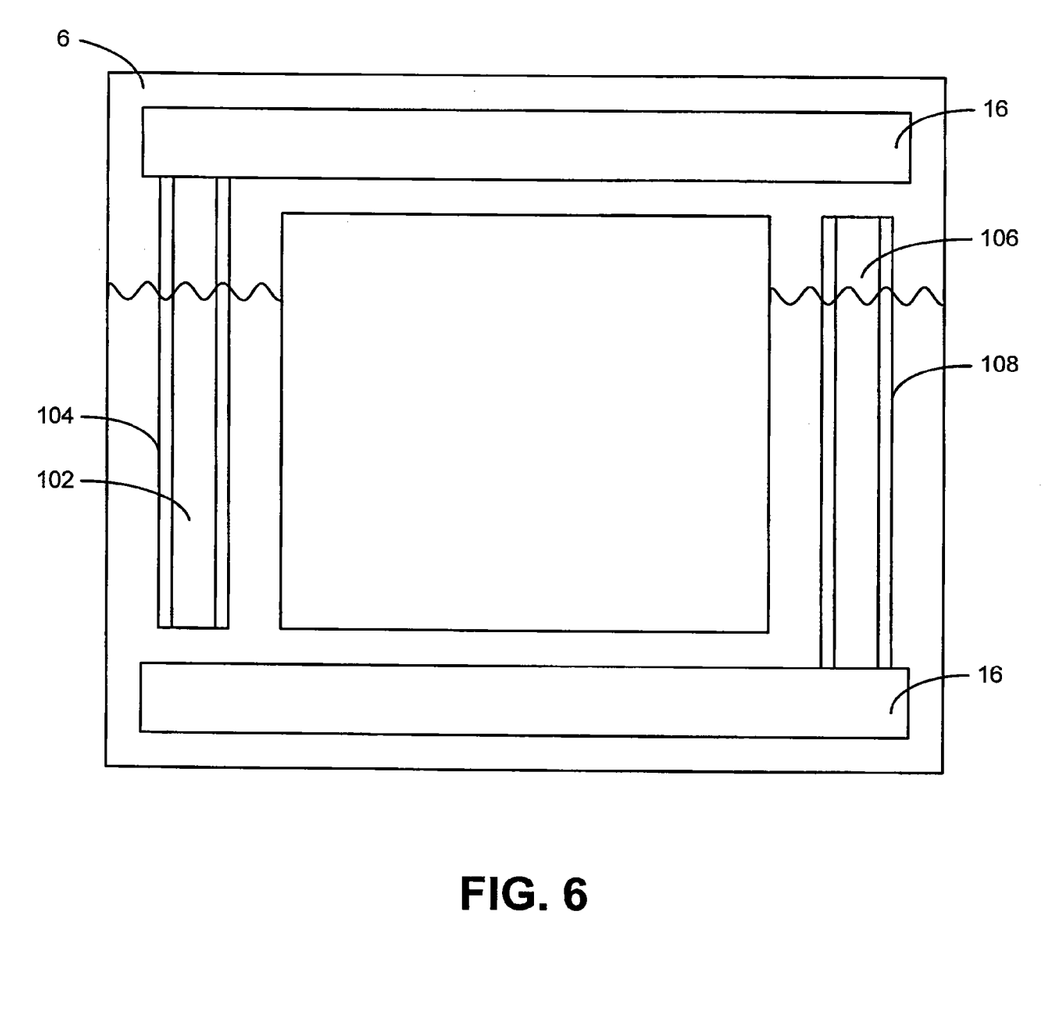
FIG. 6 illustrates an exemplary dispensing device according to an embodiment having a pair of inversely operable sleeved wicks.

With reference now to FIG. 6, accommodation of multiple outlet orientations is accomplished by a first wick 102 encased in a first sleeve 104 and a second wick 106 encased in a second sleeve 108. Wicks 102 and 106 communicate dispersible materials from reservoir 6 to emanators 16 located at opposite ends, i.e., top and bottom, of reservoir 6. Sleeves 104 and 108 are composed of an impermeable material and configured to selectively enable or block capillary transport through wicks 102 and 106. Wicks 102 and 106 extend to opposite ends of reservoir 6 such that wick 102 is in contact with dispersible materials while wick 106 is shielded by sleeve 108 in the upright orientation, and the inverse relationship exists in a second orientation.

In one embodiment, sleeves 104 and/or 108 may extend the full length of wick 102 and 106 or beyond such that wicks 102 and 106 contact dispersible materials within the sleeve. Alternatively, sleeves 104 and 108 may include any means to allow absorption of dispersible materials, for example, perforations or other openings towards one end or a bell formation around and/or past the end of wicks 102 and 106 to allow increased contact with dispersible materials in a given orientation.

Figure 7:
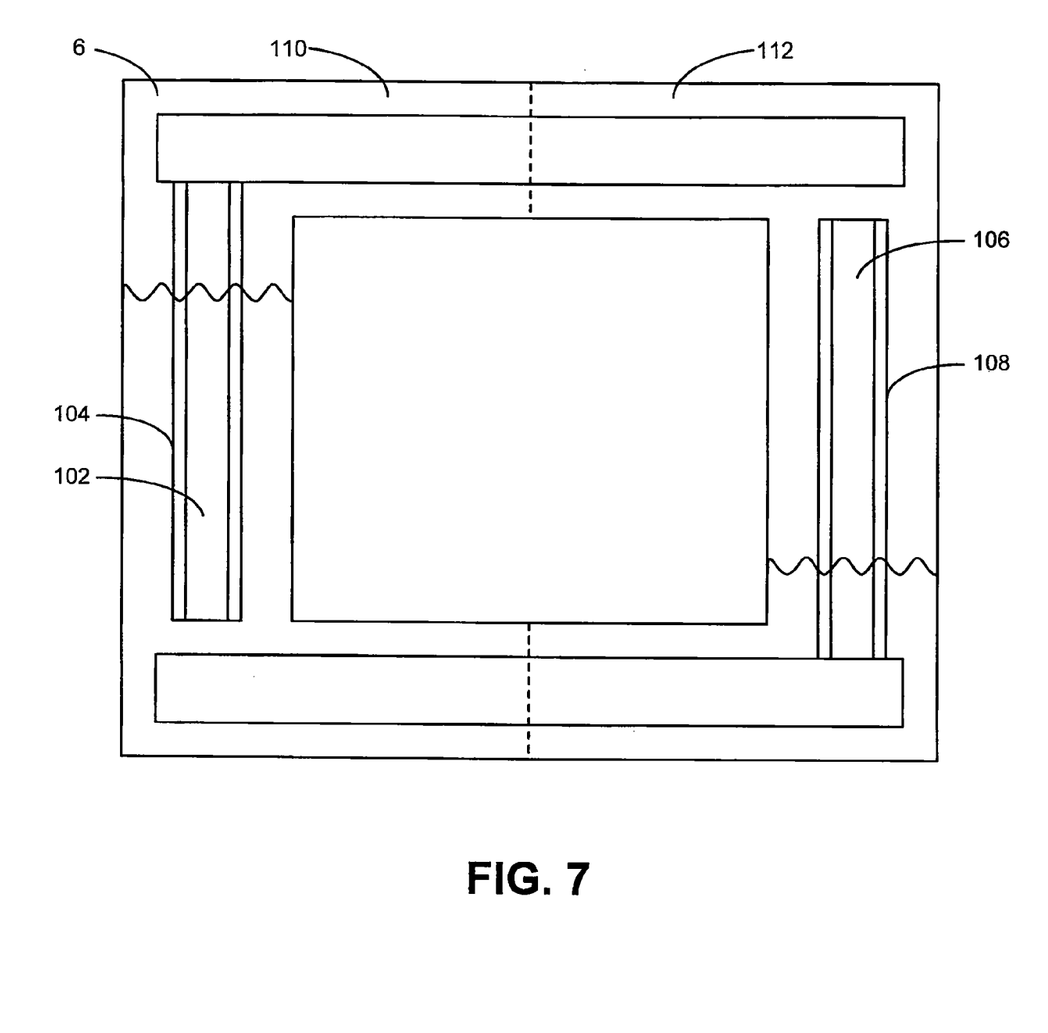
FIG. 7 illustrates an exemplary dispensing device according to an embodiment having a pair of inversely operable sleeved wicks in separate reservoir compartments.

In yet another embodiment shown in FIG. 7, two separate reservoir compartments 110 and 112 within reservoir 6 contain two distinct dispersible materials. Wick 102 is in communication with one of the two dispersible materials in a first reservoir orientation. Conversely, wick 106 is in communication with the other dispersible material in a second reservoir orientation. In other words, in an upright orientation, a portion of a wick 102 is in contact with the dispersible materials of first reservoir compartment 110 while a portion of wick 106 is maintained above the dispersible materials of second reservoir compartment 112. Inverting reservoir 6 causes a portion of wick 106 to contact the dispersible materials of second reservoir compartment 112 and further causes wick 102 to be withdrawn or isolated from the dispersible materials of first reservoir compartment 110. Wicks 102 and 106 may supply a common emanator 16 or separate emanators 16. By using two distinct dispersible materials and separate emanators 16, alternate dispersions such as varying scents may be obtained simply by reorienting reservoir 6.

As discussed above, wicks 102 and 106 need not extend beyond sleeves 104 and 108 to contact the dispersible materials. For example, in one embodiment, sleeves 104 and 108 may be dimensioned to provide an open annular chamber around a length of wicks 102 and 106. Accordingly, dispersible liquids may flow into the annular chamber up to the level of the liquid in reservoir 6. In one embodiment, wicks 102 and 106 and sleeves 104 and 108 may be configured at an angle within reservoir 6 such that liquids may flow from the annular chamber as reservoir 6 is rotated between positions. Any suitable means of allowing contact or blocking contact with dispersible materials by wicks 102 and 106 may be used in accordance with the present invention.

By configuring sleeves 104 and 108 to extend the length of wicks 102 and 106, a greater volume of reservoir 6 and/or reservoir compartments 110 and 112 may be filled with dispersible materials. In other words, because the full length of wicks 102 and 106 are shielded, the fluid level may likewise rise to the full length of a shielded wick before fluid transport begins.

Finally, while the present invention has been described above with reference to various exemplary embodiments, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices. These and other changes or modifications are intended to be included within the scope of the present invention.

What is claimed is:

1. A vapor-dispensing device of the type configured to connect to an electrical receptacle having a first outlet and a second outlet, comprising:

a removable refill body containing a volatile material;

a first heating element at a first end of said device configured to heat said volatile material to provide substantially consistent dispersion of said volatile material and activated by said device being oriented in a first upright orientation; and a second heating element at a second end of said device configured to heat said volatile material to provide substantially consistent dispersion of said volatile material and activated by said device being oriented in a second inverted orientation.

2. A vapor-dispensing device of the type configured to connect to an electrical receptacle having a first outlet and a second outlet, comprising:

a pair of prongs configured to connect to said first outlet or said second outlet wherein one prong is dimensionally distinct from the other prong; and at least one emanator configured and disposed with respect to an axis of said device to substantially consistently dispense a volatile material independent of whether said device is in a first upright orientation or in a second inverted orientation.

3. The device of claim 2, wherein said at least one emanator is disposed along the vertical length of a side portion of said device.

4. The device of claim 2, wherein said at least one emanator is disposed along substantially the full length of the periphery of said device.

5. The device of claim 2, wherein said at least one emanator includes a first emanator disposed along a top portion of said device and a second emanator disposed along a bottom portion of said device.

6. A vapor-dispensing device of the type configured to inserted into an electrical receptacle, comprising:

an outlet body having at least one pair of polar electrical prongs and at least one electrical receptacle;

a base member removably attachable to said outlet body in an upright orientation when said outlet body is in an upright orientation and when said outlet body is in an inverted orientation;

a reservoir removably attachable to said base member.

7. An improved vapor-dispensing device of the type configured to be inserted into and mimic a polar electrical receptacle, the improvement comprising:

an adapter configured to receive a first pair and a third pair of polar electrical prongs on said device, said adapter having a second pair and a fourth pair of polar electrical prongs geometrically inverted relative to said first pair and said third pair of electrical prongs for insertion into said polar electrical receptacle.

8. An improved vapor-dispensing device of the type configured to be inserted into a polar electrical receptacle, the improvement comprising:

two rotatable pairs of polar electrical prongs allowing for orientation of said device independent of a configuration of said electrical receptacle into which said device is to be inserted.

9. A vapor-dispensing device of the type configured to be inserted into a standard electrical receptacle, comprising:

an outlet body comprising:

a pair of electrical prongs for insertion into said electrical receptacle;

a first electrical outlet;

a second electrical outlet; and an electrical contact;

a base member configured to removably attach to said outlet body in an upright orientation when said outlet body is in an upright orientation and when said outlet body is in an inverted orientation by at least one of a press-fit, snap-fit and a slide-fit;

a reservoir removably attachable to said base member; and an active dispensing mechanism configured to be powered by said electrical contact when said reservoir is attached to said base member.

10. A vapor-dispensing device as in claim 1 wherein:

said first heating element is disactivated by said device being oriented in a second inverted orientation; and said second heating element is disactivated by said device being oriented in a first upright orientation.

* * * * *